United States Patent [19]

Dyer et al.

[11] Patent Number: 4,619,910

[45] Date of Patent: Oct. 28, 1986

[54] CATALYST FOR SELECTIVE CONVERSION OF SYNTHESIS GAS AND METHOD OF MAKING THE CATALYST

[75] Inventors: Paul N. Dyer, Allentown; Ronald Pierantozzi, Macungie, both of Pa.

[73] Assignee: Air Products and Chemicals, Inc., Allentown, Pa.

[21] Appl. No.: 741,403

[22] Filed: Jun. 5, 1985

[51] Int. Cl.$^4$ .................. B01J 21/04; B01J 21/06; B01J 23/46; B01J 23/74

[52] U.S. Cl. ................... 502/336; 502/325; 502/332; 502/338; 518/715

[58] Field of Search ............ 502/325, 332, 336, 338; 518/715

[56] References Cited

U.S. PATENT DOCUMENTS

| | | | |
|---|---|---|---|
| 3,980,583 | 9/1976 | Mitchell et al. | 252/430 |
| 4,088,671 | 5/1978 | Kobytimski | 260/449.6 |
| 4,219,447 | 8/1980 | Wheelock | 252/466 PT |
| 4,269,784 | 5/1981 | Doyle | 518/715 |
| 4,385,193 | 5/1983 | Bijwaard et al. | 585/310 |
| 4,393,255 | 7/1983 | Mitchell et al. | 568/902 |
| 4,400,561 | 8/1983 | Mitchell et al. | 568/902 |
| 4,413,064 | 11/1983 | Beuther et al. | 518/715 |
| 4,493,905 | 1/1985 | Beuther et al. | 502/325 |
| 4,499,209 | 2/1985 | Hoek et al. | 502/242 X |
| 4,542,122 | 9/1985 | Payne et al. | 518/715 X |

OTHER PUBLICATIONS

"The Fischer-Tropsch and Related Syntheses", Wiley, 1951, H. H. Storch et al.
Catalysis Review Science and Engineering, Poutsma, 1980, Kolbel et al., "Assessment of Advanced Process Concepts for the Liquefaction of Low $H_2$/CO Ratio Synthesis Gas".

*Primary Examiner*—W. J. Shine
*Attorney, Agent, or Firm*—Willard Jones, II; James C. Simmons; E. Eugene Innis

[57] ABSTRACT

A Fischer-Tropsch (F-T) catalyst, a method of making the catalyst and an F-T process utilizing the catalyst by which synthesis gas, particularly carbon-monoxide rich synthesis gas is selectively converted to higher hydrocarbons of relatively narrow carbon number range. In general, the selective and notably stable catalyst, consists of an inert carrier first treated with a Group IV B metal compound (such as zirconium or titanium), preferably an alkoxide compound, and subsequently treated with an organic compound of an F-T metal catalyst, such as cobalt, iron or ruthenium carbonyl. Reactions with air and water and calcination are specifically avoided in the catalyst preparation procedure.

18 Claims, 1 Drawing Figure

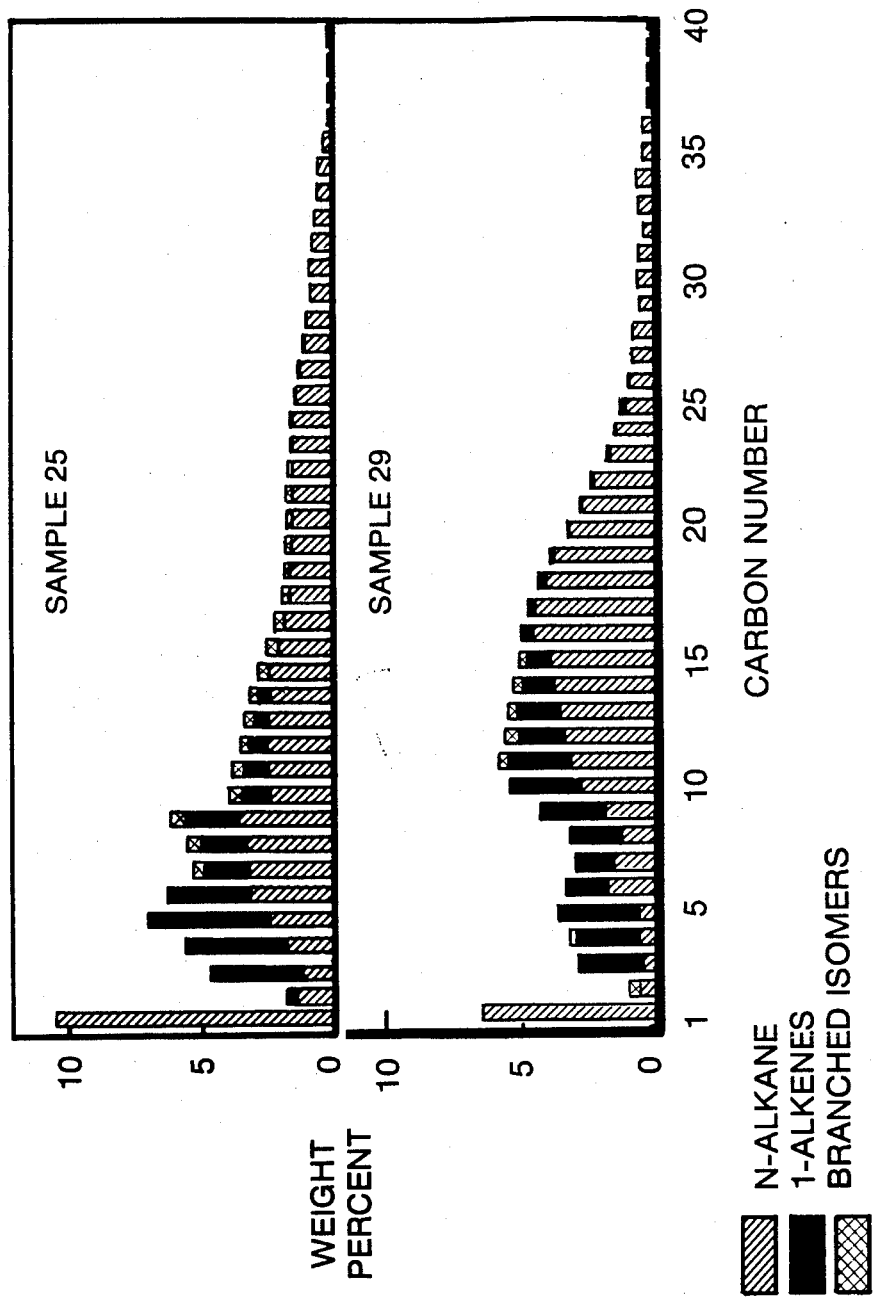

CATALYST FOR SELECTIVE CONVERSION OF SYNTHESIS GAS AND METHOD OF MAKING THE CATALYST

This invention was made under DOE Contract No. De-AC22-80PC30021 and is subject to government rights arising therefrom.

TECHNICAL FIELD

This invention relates to a process for the selective conversion of synthesis gas to hydrocarbons of relatively narrow carbon number ranges and to catalysts therefor.

BACKGROUND OF THE INVENTION

Production of hydrocarbon liquid fuels from coal may be accomplished, in part, by the Fischer-Tropsch catalyzed synthesis of hydrocarbons from synthesis gas ($CO+H_2$) produced by coal gasification. The Fischer-Tropsch synthesis (or conversion), however, is unselective in nature, producing molecules with carbon numbers typically in the range 1-40 in proportions controlled by process kinetics. Process efficiency would be enhanced by selective conversion of the synthesis gas to relatively narrow carbon number range hydrocarbons within the general range of $C_4$-$C_{25}$ hydrocarbons.

Fischer-Tropsch conversion of synthesis gas has heretofore been conducted both in fixed bed, gas-solid reactors, gas entrained fluidized bed reactors and in slurry phase reactors. The former is described by H. H. Storch et al in "The Fischer-Tropsch and Related Syntheses," Wiley, 1951, while the latter is described by Kolbel et al (Catalysis Review Science and Engineering, 1980, 21, 225), Poutsma (ORNL-5635, 1980, "Assessment of Advanced Process Concepts for the Liquefaction of Low $H_2$/CO Ratio Synthesis Gas" and Deckwer et al (Industrial Engineering Chemical Process Design Developments, 1982, Volume 21, pages 222 and 231). The latter references in particular indicate the potential incentive for using high $CO/H_2$ ratio synthesis gas (sometimes referred to as "syngas") in liquid phase slurry reactors. More recently, Satterfield et al (*Industrial Engineering Chemical Process Design Developments*, 1982, Volume 21, page 465) described literature on product distribution in Fischer-Tropsch syntheses, particularly slurry reactors using iron catalysts. All of these analyses indicate that the product selectivity in such syntheses follows a predicted Schulz-Flory distribution, characterized by a chain growth probability factor (alpha), and that any reported deviations in publications concerning the Fischer-Tropsch process are probably due to experimental artifacts.

The maximum fuel product fractions predictable from the Schulz-Flory distribution, together with an indication of methane and $C_{26+}$ fraction are as follows:

Schulz-Flory Maxima

| Alpha | $C_1$ wt. % | $C_{5-11}$ wt. % | $C_{9-25}$ wt. % | $C_{26+}$ wt. % |
|---|---|---|---|---|
| | | Gasoline Range | | |
| 0.76 | 5.8 | 47.6 | 31.8 | 0.7 |
| | | Diesel Range | | |
| 0.88 | 1.4 | 31.9 | 54.1 | 12.9 |

In general, prior publications indicate that most Fischer-Tropsch (FT) products adhere to the Schulz-Flory (SF) distribution, regardless of catalyst type. Satterfield et al specifically concluded that the distribution generally held for iron based FT catalyst with values of alpha ranging from 0.55 to 0.94. Short term success in selective syngas conversion, by utilization of a proposed metal particle size effect or by use of $Co_2(CO)_8$ on alumina or Ruthenium in zeolites of selective pore size distribution, for example, has been reported by Nijs et al (*Journal of Catalysis*, 1980, Volume 65, page 328 and Blanchard, *J. C. S. Chem. Comm.*, 1979, 605. However, none of these previous attempts has produced a stable selectivity over a period of time, the observed selectivity in each case disappearing over a period of hours and reverting to the expected Schultz-Flory distribution.

In addition to the foregoing, the following patents have been considered specifically in regard to the patentability of the present invention.

U.S. Pat. No. 4,219,447-Wheelock describes a hydrocarbon reforming catalyst and the process for its preparation. The catalyst is comprised of a Group VIII metal, preferably a Group VIII noble metal, deposited on an alumina support previously treated with a solution of Group IV B compound (a compound of titanium, zirconium, or hafnium, such as an alkoxide according to the specification of this patent); for example, the alumina catalyst base is contacted with a hydrocarbon solution of zirconium propoxide. In the preparation of this catalyst according to the Wheelock patent, the alkoxide-treated alumina catalyst base is dried and calcined in a moist atmosphere, treated in an atmosphere of 50-100% relative humidity at 60°-90° F. (sufficient to form the metal oxide) and then calcined at between 800° and 1,800° F. The Group VIII metal is then impregnated into the support in the form of a salt or complex and the catalyst is dried at 150°-300° F. in the presence of nitrogen or oxygen or both, followed by calcination at 500°-1,000° F. The Group VIII metal impregnation and subsequent calcination may be conducted in the presence of oxygen or in an inert gas atmosphere.

U.S. Pat. No. 4,385,193-Bijwarrd et al relates to a process for the preparation of middle distillates by a conventional Fischer-Tropsch (FT) first stage and a hydro-reforming second stage. Suitable catalysts for the first stage are prepared by impregnation of a porous carrier, with one or more aqueous solutions of salts of FT metals and promoters. The promoters include Group IV B metals (e.g., zirconium) and the supports include alumina. A particular example is cobalt/zirconium/silicon oxide, prepared by impregnation of the silica with an aqueous solution of a cobalt and a zirconium salt, followed by drying, calcining at 500° C. and reduction at 280° C. No indication is given in the patent of any selectivity of the catalyst for the FT reaction.

U.S. Pat. Nos. 3,980,583, 4,393,225, and 4,400,561 to Mitchell et al claim catalysts for hydroformylation and the FT reaction, prepared from $SiO_2$, $Al_2O_3$, or an alumino-silicate, which may be combined with a Group IV metal oxide. The support is functionalized with an amine which binds the catalytic Group VIII metal to the surface.

In addition, it is otherwise well-known that ruthenium is useful as an FT catalyst.

Other recent literature, Basset, *J.C.S. Chem. Comm.*, 1980, 154, has shown that catalyst prepared by the deposition of [$Fe_3(CO)_{12}$] onto an inorganic oxide support such as $Al_2O_3$, MgO and $La_2O_3$ followed by thermal decomposition results in the formation of a metal catalyst with a particle size distribution centered around 14

A°. This catalyst is said to result in the selective synthesis of propylene from $H_2$ and CO with propylene selectivities as high as 40% reported. Although the catalyst gives unusual selectivity to a fairly narrow range of products, its lifetime is short. After about six hours on stream, the catalyst begins to sinter and the selectivity drops off dramatically to give a more conventional Schulz-Flory distribution of hydrocarbons.

According to *New Syntheses With Carbon Monoxide*, J. Falbe (Springer-Verlag), 1980, metallic ruthenium will catalyze the formation of very high molecular weight hydrocarbons which are similar to polyethylene and are generally referred to as polymethylene. This process, however, only results in high molecular weights when the pressure is 1,000 to 2,000 atm. (103,000 to 206,000 kPa) and at temperatures of about 200° C.

U.S. Pat. No. 2,632,014 discloses reacting carbon monoxide and hydrogen in a $CO:H_2$ molar ratio of greater than 1:1, in the presence of water and a ruthenium catalyst, at a pressure within the range of 100 to 3,000 atm. and at a temperature of 150° to 300° C. Furthermore, the pH must be maintained below about 1. The catalyst may comprise a ruthenium-containing substance deposited on a support such as alumina.

For the synthesis of hydrocarbons from carbon monoxide and hydrogen, numerous patents (such as U.S. Pat. No. 2,284,468) disclose the use of a promoter such as an oxide of vanadium, cerium, iron, thorium, cobalt, chromium, barium, strontium, calcium, manganese, magnesium, zinc, lead, molybdenum, copper, zirconium or aluminum in combination with ruthenium catalysts.

U.S. Pat. No. 4,088,671 discloses the use of a ruthenium promoted cobalt catalyst in the synthesis of higher hydrocarbons from carbon monoxide and hydrogen In a low pressure synthesis gas process the catalyst is said to result in the substantial elimination of methane in the product with a simultaneous shift to the production of a higher carbon number product having a lower olefin content. The catalyst may be applied to a suitable support material such as alumina, boria, zinc oxide, magnesia, calcium oxide, strontium oide, barium oxide, titania, zirconia and vanadia.

U.S. Pat. No. 4,269,784 discloses a homogeneous process for preparing $C_9$ to $C_{60}$ hydrocarbons from carbon monoxide and water using a water-soluble ruthenium catalyst. The ruthenium catalyst may be a simple salt such as a halide, acetylacetonate or a complex salt of the formula $[RuL_6]^n$ where L is a neutral or charged ligand and n is the charge on the complex.

British Pat. No. 2,130,113 - Hoek, et al. (published May 31, 1984, priority date Nov. 22, 1982) discloses a Fischer-Tropsch catalyst with $C_3-C_5$ selectivity. The catalyst uses a silica base, which is impregnated with an organic solution of, for example, zirconium or titanium propoxide and calcined. Cobalt is then deposited, as cobalt nitrate for example, from aqueous solution and is calcined.

U.S. Pat. Nos. 4,413,064 and 4,493,905 Beuther, et al. (filing date Oct. 13, 1981, issue dates Nov. 1, 1983 and Jan. 15, 1985, respectively) disclose a Fischer-Tropsch catalyst, selective for the production of diesel fuel, based on a gamma or eta alumina support on which is deposited (a) cobalt and a Group IV B metal salt from a non-aqueous organic impregnant solution or (b) in a two-step process, preferably without calcination, cobalt (from an aqueous solution of, for example, cobalt nitrate) and then, from a non-aqueous organic solution, a ruthenium salt and a Group IV B metal oxide, the preferred oxides including $ZrO_2$ and $TiO_2$.

Notwithstanding the foregoing teachings, there remains a need for a selective, stable process and catalyst by which synthesis gas may be selectively converted to narrow carbon number range hydrocarbons and it is the general objective of the present invention to provide a stable catalyst and process effective to selectively produce such products, preferably at mild process conditions.

SUMMARY OF THE INVENTION

In accordance with the present invention, synthesis gas, and particularly CO-rich syngas (i.e. with a $CO:H_2$ mole ratio of 1:1 to 3:1), is subjected to Fischer-Tropsch catalysis, preferably in an otherwise conventional slurry phase reaction, with a stable enhanced selectivity for conversion of the synthesis gas to hydrocarbon product of relatively narrow carbon number ranges by the utilization of a Fischer-Tropsch catalyst formulated as follows:

Solid alumina catalyst base particles (or alternatively other metal oxide catalyst base particles such as silica or magnesium oxide) are treated in the absence of air and water with an organic solution of a decomposable organic compound or salt of a Group IV B metal (preferably zirconium but possibly titanium or hafnium) alkoxide (preferably propoxide). The treated catalyst particles are then in turn impregnated with an organic solution of a decomposable organic compound or salt (or mixtures thereof) of a a product selective catalytic metal, namely, cobalt, iron or ruthenium. The preferred decomposable compounds are the carbonyls of cobalt, iron or ruthenium.

The catalyst preparation conditions, the compounds utilized in catalyst preparation, and the slurry phase FT reaction conditions all have some effect on the selectivity of the catalyst in the FT reaction. In general, the iron carbonyl treated catalyst tends to be selective for $C_4$ and $C_5$ hydrocarbons, the ruthenium treated catalyst tends to be selective for gasoline range hydrocarbons, such as $C_5-C_{11}$ compounds and the cobalt-treated catalyst tends to be selective for the diesel fuel range of product, namely $C_9-C_{25}$.

As contrasted with most of the prior art process and catalysts discussed above, calcination, oxidation, and water reaction (hydrolysis) with the catalyst is specifically avoided. The final step in catalyst preparation in each case is essentially a reduction or preactivation of the catalyst in a fixed bed reactor, exposing the catalyst to synthesis gas at slightly elevated pressure and temperature, on the order of 100-200 psig and stagewise temperature increases from about 220°-270° C.

The Group IV B metal comprises 1-20 weight % of the catalyst and the amount of FT catalytic metal (cobalt, iron or ruthenium) is in the range of 0.1-10 weight percent of the catalyst.

For a better understanding of this invention, reference may be made to the detailed description thereof which follows, taken together with the subjoined claims.

BRIEF DESCRIPTION OF THE FIGURE

The Figure is a graphical illustration of product distribution for two samples discussed in Example 1.

DETAILED DESCRIPTION OF THE INVENTION

The oxide support materials which may be used in the catalyst of the invention are those inorganic metal oxides which are typically used as catalytic support materials. For example, such support materials include the oxides of the metals of Groups II, III, IV, V, and VIA of the Periodic Table. The oxides of the metals of Groups II, III B and IV B are preferred. These include alumina, boria, zinc oxide, magnesia, calcium oxide, strontium oxide, barium oxide, titania, zirconia and vanadia. The most preferred support is alumina. A combination of metal oxides, such as silica-alumina, can be employed. The supports can be synthetically prepared or can be naturally occurring support materials, such as the naturally occurring clays. Specific examples of other suitable supports include kieselguhr, diatomaceous earth, zeolites, silica, thoria, zirconia, and mixtures of the above.

In making the catalyst of the present invention, the above-referenced support material is treated in the absence of oxygen and water, with a non-aqueous, typically organic, solution of an organic compound or salt of a Group IV B xetal (zirconium, titanium or hafnium or a combination thereof) compound, preferably an organo compound of zirconium to provide a support containing from 1 to 20 wt. % of the Group IV B metal. The most preferred material is an organo-zirconium compound.

Preferably, the organic radical is an alkoxide radical such as ethoxide, propoxide, iso-propoxide and the like. Although alkyl compounds may also be used, they are likely to be less effective. In any event, the organic part of the compound should be decomposable, i.e., adapted to be driven off at moderate elevated temperature (below that of the syngas conversion reaction) to leave a dispersed metallic residue. Examples of suitable organo-Group IV B metal compounds useful in the practice of the invention include zirconium propoxide, zirconium ethoxide, titanium isopropoxide, titanium ethoxide, hafnium propoxide and the like, of which zirconium propoxide is preferred in the present invention. Typically the Group IV B metal compound is dissolved in a suitable solvent, such as cyclohexane, which is non-aqueous and non-reactive with the metal and the catalyst substrate. The catalyst support material is mixed with the solution, then removed and exposed to a vacuum to remove remaining solvent.

Conventional catalyst preparation techniques such as mixing the solid catalyst support to the point of "incipient wetness" with the impregnant is used both with the Group IV B metal treatment and in the subsequent F-T metal treatment.

The Group IV B metal compound treated catalyst is then treated in the absence of oxygen and water with a solution of a decomposable compound, typically an organometallic compound, of a selective Fischer-Tropsch catalyst metal, particularly including cobalt, iron or ruthenium. Other than carbonyls, which are preferred, compounds which may be used include acetate, pentanedionate, or other organic complexes or organometallic compounds of cobalt, iron or ruthenium, which decompose at moderate temperature (below that of the syngas conversion process) to leave a metallic residue. Preferably also, the amount of Fischer-Tropsch catalytic metal in the catalyst following such impregnation and drying is in the range of 0.1-10 weight percent.

For impregnation of the catalyst, the metal compound is also dissolved in a suitable organic solvent such as cyclohexane. This impregnating solution is stirred with the previously treated oxide support material catalyst. After thorough mixing, the mixture is dried (but not calcined). Preferably, drying is performed in vacuum at room temperature.

Thereafter, the catalyst may be conditioned for use by transfer in the absence of oxygen and water into a reactor, and introduction of the Fischer-Tropsch reaction media.

The catalyst of the present invention, produced as described above, may be utilized in a process, also in accordance with the present invention, to prepare high molecular weight hydrocarbons selectively with respect to the carbon number range of the hydrocarbons. The Fischer-Tropsch reaction conditions with which this catalyst may be used are generally relatively mild and may be selected so as to produce relatively low yields of methane while avoiding extremely high pressure process conditions.

In general, the Fischer-Tropsch function of the catalyst is combined with the polymerization function of the Group IV B compound impregnant on the catalyst.

The process then comprises reacting a hydrogen-carbon monoxide synthesis gas, preferably in a slurry phase reaction, with a CO to hydrogen ratio in the range of 1:2 to 3:1, preferably about 1.4:1 to 2:1, at a space velocity of about 200 hour$^{-1}$ to about 1000 hour$^{-1}$, preferably about 300 hour$^{-1}$ to about 600 hour$^{-1}$, over the catalyst of this invention, for a time sufficient to effect the production of the desired higher hydrocarbons under the reaction conditions. Reaction conditions include a temperature in the range of 200° to 350° C., preferably about 230° to 275° C. and at a pressure of about 100 to 1000 psig, preferably about 250 to 450. While the above reaction conditions may have to be adjusted accordingly, it is possible also in some circumstances to utilize an equivalent amount of carbon dioxide for the carbon monoxide in the synthesis gas.

Specific examples of the present invention, utilizing cobalt carbonyl, ruthenium carbonyl and iron carbonyl, respectively, with zirconium propoxide and alumina catalyst support, are described below in Examples 1-3, together with representative data therefrom in numerous experimental runs utilizing materials of these examples. These data are set forth in Tables I-V.

EXAMPLE 1

Catalyst Preparation

$Zr(OC_3H_7)_4$ was reacted by mixture with $Al_2O_3$ in cyclohexane in an inert atmosphere until a preselected proportional of $Zr(OC_3H_7)_4$ was deposited on the alumina. The quantity of $Zr(OC_3H_7)_4$ is selected such that essentially all of the Al-OH groups on the $Al_2O_3$ are combined with Zr compounds, in accordance with the following reaction:

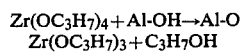

[Co₂(CO)₈]/Zr(OC₃H₇)₄/Al₂O₃

[Co$_2$(CO)$_8$] dissolved in hexane/toluene (volume ratio=1:1) was added to the Zr(OC$_3$H$_7$)$_4$-treated alumina prepared above (after it had been dried in vacuo) in several steps using incipient wetness methods in the absence of oxygen or water. After each addition of [Co$_2$(CO)$_8$] the solvent was removed in vacuo along with any [Co$_2$(CO)$_8$] that did not react with the surface.

Catalyst Testing Results

The catalyst was transferred to a fixed bed reactor, under an inert gas such as N$_2$ in the absence of oxygen or water or preactivated in the gas phase using 20% 1:1 CO/H$_2$ in N$_2$ at 175 psig and a GHSV (Gas Hourly Space Velocity) of 136 h$^{-1}$ (volume gas-slurry/volume catalyst bed/hour), raising the bed temeprature in 10° C. stages from 220° to 270° C. After cooling in N$_2$, the activated catalyst (particle size <45 μm) was slurried in deoxygenated white paraffin oil (as commercially available from Fisher Scientific) and transferred to a 300 mL slurry reactor under a N$_2$ atmosphere. The final loading was 158 mL of a 15.07 wt % slurry containing 21.33 g of activated catalyst.

The slurried catalyst was then contacted with CO/H$_2$ (at mole ratios of about 1:1 and 2:1) at 217°–250° C., 300–500 psig, and 310–350 H$^{-1}$ GHSV using stir speeds of 1200 and 1600 min$^{-1}$. Several main sample points, with associated operating conditions, conversions, and feed ratios are listed in Table I.

III. These rates may also be considered rates of formation for the various product fractions.

From this and other data, it is apparent that the catalyst was immediately active in the slurry phase at 220° C., 314 psig and 0.97 CO:H$_2$, with a CO conversion of 12.85% (fractional conversion×100) corresponding to an activity of 17.24 mol syngas/kg cat/h (sample 4). Initially, the hydrocarbon product was close to a standard Schulz-Flory distribution, except for a higher CH$_4$ yield of 15.8% and a low C$_2$. Approximately 48% of the deficiency in the C$_2$ hydrocarbon yield was accounted for by the production of C$_2$ oxygenates.

While these initial conditions were held essentially constant for 49 hours, the product distribution moved to higher molecular weight (sample 8). Although the overall activity decreased linearly by 15.4% over this period, the rates of formation of the C$_{12-17}$ and C$_{18+}$ fractions remained constant and increased respectively (Table III) corresponding to a progressive increase in the degree of polymerization from 0.73 to 0.80.

After 169 hours, with reaction conditions at 247° C. and 0.97 CO/H$_2$, a catalyst activity of 44.9 mol syngas/kg cat/h, was recorded corresponding to an overall conversion of 41.8% and a H$_2$ conversion of 56.3% (sample 25). However, product distribution (up to C$_{36}$) approximated that predicted by the Schulz-Flory at c=.87. Although this value of degree of polymerization is the theoretical optimum for the maximum yield of C$_{10-20}$ product (40 wt %) from a standard distribution, the anomalously high CH$_4$ yield of 10.7 wt % reduced

TABLE I

Slurry Run Summary
(Example 1)
15.07 wt. % Slurry of 18.0% [Co$_2$(CO)$_8$]/Zr(OPr)$_4$/Al$_2$O$_3$

| Sample # | Time h | p psig | T °C. | GHSV h$^{-1}$ | Stir Speed min$^{-1}$ | Fractional Conversion CO + H$_2$ | CO | H$_2$ | Feed Ratio CO:H$_2$ |
|---|---|---|---|---|---|---|---|---|---|
| 4 | 25.4 | 314 | 219.9 | 321.6 | 1200 | 0.201 | 0.128 | 0.272 | .97 |
| 8 | 48.9 | 312 | 218.9 | 318.5 | 1200 | 0.178 | 0.106 | 0.247 | .96 |
| 25 | 169.4 | 300 | 246.5 | 324.9 | 1600 | 0.418 | 0.269 | 0.563 | .97 |
| 29 | 193.3 | 302 | 250.0 | 348.3 | 1600 | 0.266 | 0.157 | 0.483 | 1.98 |

TABLE II

Summary of Slurry Phase Product Distribution
Data for Co$_2$(CO)$_8$/Zr/Al$_2$O$_3$
(Example 1)

| Samples # | Product Distribution (wt. %) | | | | |
|---|---|---|---|---|---|
| | C$_1$ | C$_2$–C$_4$ | C$_5$–C$_{12}$ | C$_{12}$–C$_{17}$ | C$_{18+}$ |
| 4 | 15.76 | 25.42 | 48.43 | 10.75 | 1.66 |
| 8 | 15.99 | 23.64 | 43.50 | 13.81 | 4.32 |
| 25 | 10.74 | 12.13 | 38.77 | 18.76 | 19.30 |
| 29 | 5.71 | 6.34 | 22.68 | 28.77 | 33.50 |

TABLE III

CO Conversion Rates Into Product Fraction (10$^{-4}$ mol/min)
(Example 1)

| Sample # | C$_1$ | C$_2$–C$_4$ | C$_5$–C$_{11}$ | C$_{12}$–C$_{17}$ | C$_{18+}$ | Total Hydrocarbons |
|---|---|---|---|---|---|---|
| 4 | 2.55 | 4.61 | 7.72 | 1.97 | 0.39 | 17.24 |
| 8 | 2.19 | 3.62 | 6.61 | 1.95 | 0.66 | 14.58 |
| 25 | 4.38 | 5.55 | 16.66 | 8.05 | 9.68 | 44.32 |
| 29 | 2.15 | 2.69 | 9.19 | 12.29 | 15.67 | 41.99 |

Product distribution data for the Samples listed in Table I are summarized in Table II. In addition, the rates of CO conversion into various product fractions for the samples referred to in Table II are listed in Table the C$_{10-20}$ fraction to 30.6 wt %.

Note that Samples 4, 8 and 25 are illustrative of reaction conditions including a CO:H$_2$ ratio actually slightly below 1:1.

When the CO/H$_2$ ratio was increased to 1.98 at comparable temperatures, further significant departures from the expected SF distribution appear. For example, the CH$_4$ yield was reduced from 10.7 to 5.7 wt % (Sample 25 compared to Sample 29). With this reduced formation of lighter fractions and corresponding increased rates for C$_{12-17}$ and C$_{18+}$, a lower overall activity of 30.65 mol syngas/kg cat/h was obtained. The deviation from the Schulz-Flory distribution in the diesel fuel range, as shown for example by sample 29, demonstrate selective conversion to hydrocarbons in the diesel fuel range. This is indicated specifically by the C$_{12-17}$ and C$_{18+}$ product fractions (28.77 and 30.50 wt % respectively), and the overall C$_9$–C$_{25}$ product fraction (72.2 wt %), all of which is also illustrated in the graphical indication of product distribution for Samples 25 and 29 in the Figure.

In general, this and other data demonstrates selective conversion, at a high CO:H$_2$ ratio, of synthesis gas to hydrocarbons in the diesel fuel carbon number range. The reduction of product above C$_{26}$ (as compared to an expected Schulz-Flory distribution) is an important feature of this catalyst for operation in the slurry phase. The buildup of undistilled heavier product in the slurry phase, and the need to withdraw slurry and catalyst to maintain a constant level, is minimized.

The effectiveness of this invention with $Co_2(CO)_8/Zr/Al_2O_3$ is particularly notable. This catalyst is highly selective for diesel fuel (typically 67% $C_9$–$C_{25}$, when contacted with 2:1 $CO/H_2$ syngas in a slurry reactor system). The 67.3 wt % product obtained in the $C_9$–$C_{25}$ range represents a 25% increase over what was previously thought to be a limit of 54.1% imposed by the S-F distribution. This is particularly important, since the F-T product, with its potential for high n-alkane yield, appears to be particularly well suited for the production of diesel fuel. F-T catalysts prepared in accordance herewith, therefore, can overcome the limitations on the yield of product fraction, e.g. fuels or lower molecular weight oxygenates, that were previously thought imposed by the standard S-F distribution. The selectivity of the catalyst of this invention is retained as a function of time, and deactivation rates are low. The catalysts of this invention are also capable of accepting directly a high $CO/H_2$ ratio synthesis gas such as is produced by advanced generation coal gasifiers. The combination of selectivity, maintenance of that selectivity and the integration of the indirect liquefaction stage with the coal gasification stage that is made possible by the ability to accept CO-rich syngas directly without external shift, improves greatly the overall energy efficiency of the process.

EXAMPLE 2

Catalyst Preparation $[Ru_3(CO)_{12}]/Zr(OC_3H_7)_4/Al_2O_3$

The catalyst was prepared by adding a hexane solution of $[Ru_3(CO)_{12}]$ to the $Zr(OC_3H_7)_4$ support prepared as described in Example 1 above. The solvent was then removed in vacuum and the catalyst protected from air and water.

Catalyst Testing

The catalyst was activated in a fixed bed reactor by reaction with $CO+H_2$ prior to slurrying in the oil in the absence of air. The catalyst was treated with $CO/H_2$ (1:1) at GHSV=415 hours, P=350 psig and T=240° C. This activation was continued for 190 minutes. The catalyst was then loaded into the oil under a $N_2$ atmosphere. The resulting slurry contained 12.22 wt % catalyst. The product distributions and catalyst testing results are summarized in Table IV.

TABLE IV
Example 2
Summary of Catalyst Testing Results for
$[Ru_3(CO)_{12}]/Zr(OPr)_4/Al_2O_3$

| Sample # | $CO/H_2$ | T (°C.) | P (psig) | CO conv (%) | $C_1$ | $C_2$–$C_4$ | $C_5$–$C_{11}$ | $C_{12}$–$C_{17}$ | $C_{18+}$ |
|---|---|---|---|---|---|---|---|---|---|
| 8  | 1.047 | 250   | 310 | 6.56  | 26.09 | 27.80 | 32.87 | 7.62  | 6.13 |
| 23 | 1.019 | 280   | 300 | 22.63 | 27.00 | 22.94 | 35.65 | 9.96  | 4.46 |
| 37 | 2.984 | 279.5 | 305 | 6.71  | 19.59 | 23.15 | 40.63 | 8.70  | 7.91 |
| 41 | 1.230 | 281   | 500 | 29.21 | 20.55 | 20.55 | 44.87 | 11.07 | 2.96 |
| 53 | 2.965 | 279   | 750 | 10.43 | 11.55 | 18.07 | 51.15 | 14.06 | 5.17 |

In summary, when contacted with CO-rich synthesis gas, this catalyst demonstrated a selectivity to produce high yields of gasoline range hydrocarbons, $C_5$–$C_{11}$. There was also a sharp cutoff at $C_{28}$–$C_{30}$, preventing the formation of heavy waxes. This is an important feature of the catalyst forming phase operation, as it minimizes the need for withdrawal of slurry and catalyst from the reactor.

EXAMPLE 3

Catalyst Preparation and Testing $Fe_3(CO)_{12}/Zr(OPr)_4/Al_2O_3$

This catalyst was prepared in a manner analogous to $[Ru_3(CO)_{12}]/Zr(OPr)_4/Al_2O_3$ and protected from air at all times. Fixed bed catalytic reaction data and product distribution is shown in Table V.

TABLE V
(Example 3)

Catalyst: $[Fe_3(CO)12]/Zr(OPr)_4/Al_2O_3$  $H_2/CO$: 1
Time on Stream: 169 h    Conversion (%)
Temperature: 270.4° C.
Pressure: 300 psig    CO: 3.24% conversion
GHSV: 201 $h^{-1}$ Fixed Bed Reactor

| | n-alkanes | | 1-alkene | | Branched Isomers | |
|---|---|---|---|---|---|---|
| Carbon # | Wt. % | Mole % | Wt. % | Mole % | Wt. % | Mole % |
| 1 | 6.73  | 18.88 | —     | —     | —    | —    |
| 2 | 1.27  | 1.01  | 11.13 | 18.01 | —    | —    |
| 3 | 0.53  | 0.54  | 8.13  | 8.77  | —    | —    |
| 4 | 6.40  | 4.99  | 22.97 | 18.58 | —    | —    |
| 5 | 23.41 | 14.70 | 3.99  | 2.58  | 0.83 | 0.52 |
| 6 | 3.54  | 1.86  | 3.21  | 1.73  | —    | —    |
| $CH_3OCH_3$ | 1.16 | 1.06 | | | | |
| $CH_3OH$ | 1.92 | 2.52 | | | | |
| $C_3H_7OH$ | 4.77 | 3.34 | | | | |

From the foregoing, it is seen that the treatment of the alumina surface with $Zr(OC_3H_7)_4$ results in a support which, when impregnated with iron as the Fischer-Tropsch catalytic metal, gives a selective F-T catalyst, with selectivity centered in the $C_4$–$C_5$ range.

While the foregoing data are illustrative, the carbon number range of the product and the type of carbon products in the present invention may be varied not only by modification of reaction conditions but also by the selection of F-T catalyst metals or metals placed on the catalyst surface, and also on the ratio of FT catalyst metal to Group IV B metal to catalyst substrate.

The concentrations of Group IV B and catalytic metals in the catalysts used in these examples was: (weight % of total catalyst after final drying and before activation.)

| | Zr | Co | Ru | Fe |
|---|---|---|---|---|
| Example 1 | 11.87 | 6.22 | | |
| Example 2 | 16.32 | | 4.8 | |
| Example 3 | 27.52 | | | 0.54 |

The selectivity of the catalyst of this invention is retained as a function of time, and deactivation rates are low. The catalysts of this invention are also capable of accepting directly a high $CO/H_2$ ratio synthesis gas, such as is produced by advanced generation coal gasifiers. The combination of selectivity, maintenance of that selectivity and the integration of the indirect liquefaction stage with the coal gasification stage that is made possible by the ability to accept CO-rich syngas directly without external shift, improves greatly the overall energy efficiency of the process.

STATEMENT OF INDUSTRIAL APPLICATION

This invention provides a process for preparing valuable higher hydrocarbon products by reacting a mixture of hydrogen and carbon monoxide over specific catalysts comprised of Fischer-Tropsch catalytic metal compounds impregnated on metal Group IV B compound treated inert catalyst solids. Hydrocarbons within preselected carbon number ranges may be produced and the enhanced selectivity of the process may be maintained over a period of time. The present invention also includes the catalyst for this process and the method of making this catalyst.

We claim:

1. Method of making a catalyst comprising the following steps:
   (a) treating an inert, inorganic metal oxide catalyst base material with a nonaqueous solution of a decomposable salt or organic compound of a group IVB metal and removing remaining said nonaqueous solution;
   (b) impregnating the product of Step (a) with a nonaqueous solution of a decomposable salt or organic compound of a Fischer-Tropsch metal catalyst from the group consisting of cobalt, iron or ruthenium, and removing remaining said nonaqueous solution; and
   (c) exposing the product of Step (b) to a reducing atmosphere; all while maintaining said material and said products under conditions sufficient to avoid hydrolysis, oxidation, and calcination thereof.

2. Method, as recited in claim 1 wherein said base material is alumina.

3. Method, as recited in claim 1, wherein said Group IV B metal compound is zirconium, titanium or hafnium alkoxide.

4. Method, as recited in claim 1, wherein said cobalt, iron or ruthenium compound is a carbonyl.

5. Method as recited in claim 1, wherein said base material is alumina, said Group IV B metal compound is zirconium, titanium or hafnium alkoxide, and said cobalt, iron or ruthenium compound is a carbonyl.

6. Method as recited in claim 5, wherein said Group IV metal compound is zirconium alkoxide.

7. Method, as recited in claim 5, wherein said Fischer-Tropsch metal catalyst is cobalt.

8. Method, as recited in claim 5, wherein said Fischer-Tropsch metal catalyst is iron.

9. Method, as recited in claim 5, wherein said Fischer-Tropsch metal catalyst is ruthenium.

10. A catalyst produced by the method recited in claim 1.

11. A catalyst produced by the method recited in claim 2.

12. A catalyst produced by the method recited in claim 3.

13. A catalyst produced by the method recited in claim 4.

14. A catalyst produced by the method recited in claim 5.

15. A catalyst produced by the method recited in claim 6.

16. A catalyst produced by the method recited in claim 7.

17. A catalyst produced by the method recited in claim 8.

18. A catalyst produced by the method recited in claim 9.

* * * * *